United States Patent [19]

Kaugars

[11] 4,094,906
[45] June 13, 1978

[54] ALKANOYL CHLORIDE PHENYLHYDRAZONES

[75] Inventor: Girts Kaugars, Cooper Township, Kalamazoo County, Mich.

[73] Assignee: The Upjohn Company, Kalamazoo, Mich.

[21] Appl. No.: 505,965

[22] Filed: Sep. 16, 1974

Related U.S. Application Data

[62] Division of Ser. No. 326,804, Jan. 26, 1973, Pat. No. 3,870,505, which is a division of Ser. No. 874,976, Nov. 7, 1969, Pat. No. 3,745,215.

[51] Int. Cl.$^2$ ............................................. C07C 109/14
[52] U.S. Cl. ............................. 260/566 B; 260/561 H
[58] Field of Search ........................ 260/566 B, 566 D

[56] References Cited

U.S. PATENT DOCUMENTS

| 2,970,941 | /1961 | Holbrook | 424/327 |
|---|---|---|---|
| 3,847,987 | /1974 | Boesch | 260/566 B |

OTHER PUBLICATIONS

Huisgen et al, Ann. vol. 591 pp. 200-231 (1955).
Humphries et al., J. Chem. Society (London) vol. 127, pp. 1304-1307 (1925).
Hegarty et al, J. Org. Chem. vol. 33 pp. 753 (1968).
Chem. Abstr. vol. 49 col. 13140(d).
Hegarty et al, J. Org. Chem. vol. 33 pp. 753-762 (1968).

*Primary Examiner*—Gerald A. Schwartz
*Attorney, Agent, or Firm*—William G. Jameson; Sidney B. Williams, Jr.

[57] ABSTRACT

Certain alkanoyl chloride phenylhydrazones have been found to be active against insects and mites, and also active as herbicides. The phenylhydrazone ring can be substituted. Suitable substituent groups are halogen atoms, the nitro group, the trifluoromethyl group, and alkyl groups of from 1 to 6 carbon atoms, inclusive. The compounds are prepared by reacting an alkanoic acid phenylhy-drazide with phosphorus pentachloride to obtain an alkanoyl chloride (dichlorophosphinyl)-phenylhydrazone intermediate that is reacted with phenol to produce the desired alkanoyl chloride phenylhydrazone. Certain compounds can be prepared by direct chlorination of an alkanaldehyde phenylhydrazone. Some of the compounds are novel. Methods of use and compositions are described.

20 Claims, No Drawings

ALKANOYL CHLORIDE PHENYLHYDRAZONES

CROSS REFERENCE TO RELATED APPLICATIONS

This application is a division of my copending application Ser. No. 326,804, filed Jan. 26, 1973, now U.S. Pat. No. 3,870,505, issued Mar. 11, 1975, which is a division of then copending application Ser. No. 874,976, filed Nov. 7, 1969, which issued as U.S. Pat. No. 3,745,215 on July 10, 1973.

SUMMARY OF INVENTION

This invention pertains to a new method for combating pestiferous insects and mites, new insecticidal and miticidal compositions, a new method for controlling weeds, new herbicidal compositions, and new chemical compounds. The invention is more particularly directed to alkanoyl chloride phenylhydrazones useful for combating insects and mites and for controlling weeds, and to new insecticidal and miticidal, and herbicidal compositions having as the essential active ingredient these alkanoyl chloride phenylhydrazones. Particular attention is directed to new alkanoyl chloride (trihalophenyl) hydrazones and new pivaloyl chloride phenylhydrazones.

The newly recognized insecticidal and miticidal, and herbicidal alkanoyl chloride phenylhydrazones have the general structural formula

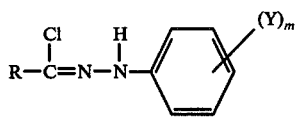

wherein R is alkyl of from 1 to 5 carbon atoms, inclusive; Y is alkyl of from 1 to 6 carbon atoms, inclusive, halogen; trifluoromethyl and nitro; $m$ is an integer from 0 to 3, inclusive; there may be no more than one nitro group in the molecule, and the Y's may be selected independently when $m$ is 2 or 3.

DETAILED DESCRIPTION OF THE INVENTION

The insecticidal and miticidal, and herbicidal alkanoyl chloride phenylhydrazones of this invention are prepared by reacting a selected alkanoic acid phenylhydrazide with phosphorus pentachloride, reacting the resulting, corresponding alkanoyl chloride (dichlorophosphinyl)phenylhydrazone with phenol, and recovering the desired alkanoyl chloride phenylhydrazone. The reaction steps are shown diagrammatically as follows:

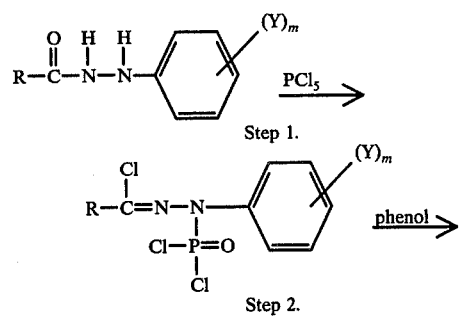

-continued

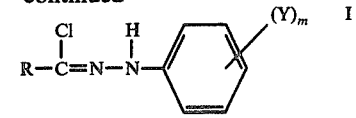

wherein R, Y and $m$ are as given above.

Step 1. of the foregoing process proceeds when the alkanoic acid phenylhydrazide starting compound and the phosphorus pentachloride are mixed in the presence of a reaction medium at a temperature in the range of about 5° C. up to about the boiling point of the reaction medium although higher and lower temperatures can be used. The reaction rate will be decreased at low temperatures, and a pressure vessel would be needed to effect reaction temperatures above the boiling point at atmospheric pressure. In accordance with a preferred embodiment, the initial reaction mixture is heated.

Appropriate reaction media include, for example, the chlorinated hydrocarbon solvents, aliphatic or aromatic hydrocarbon solvents, and ethers. Representative specific ones are carbon tetrachloride (preferred), methylene chloride, chloroform, 1,2-dichloroethylene, benzene, toluene, technical hexane, diethyl ether, and dioxane.

The process can be practiced without isolating the alkanoyl chloride (dichlorophosphinyl)phenylhydrazone intermediate when three equivalents or more of phenol are added to the initial reaction mixture after it has been cooled to about 0° to 25° C. The phenol reacts with the alkanoyl chloride (dichlorophosphinyl)phenylhydrazone intermediate to produce triphenyl phosphate, and the desired alkanoyl chloride phenylhydrazone is then recovered and purified by conventional methods. Illustratively, the solvent medium is removed, e.g., by evaporation, and the usually oily mixture that is obtained is heated to distil the alkanoyl chloride phenylhydrazone. Alternatively, the desired alkanoyl chloride phenylhydrazone, if a solid, can be separated from the residual triphenyl phosphate by filtration or by chromatographic techniques. The compound is purified by recrystallization.

The alkanoic acid phenylhydrazide starting compounds are known or can be readily prepared by known methods. According to one method an alkanoyl chloride is reacted with a phenylhydrazine, using the procedures described by J. Hausknecht, Chem. Ber. 22, p. 324 (1889), and E. Bamberger and W. Pemsel, Chem. Ber. 36, p. 359 (1903). Another method described in U.S. Pat. No. 2,912,461, issued Nov. 10, 1959, can be utilized to react an alkanoate ester and a phenylhydrazine. Still another method described by W. Autenrieth and G. Thomae, Chem. Ber. 57, p. 423 (1924) can be used to react an alkanoic acid anhydride with a phenylhydrazine to produce the corresponding alkanoic acid phenylhydrazide. Preparation I hereinafter illustrates a conventional method for making alkanoic acid phenylhydrazide starting compounds.

The insecticidal and miticidal, and herbicidal alkanoyl chloride phenylhydrazones of this invention (compounds according to Formula I) can also be prepared by chlorinating an alkanaldehyde phenylhydrazone. Chlorination of an alkanaldehyde phenylhydrazone can be accomplished as described by J. E. Humphries, H. Humble and R. Evans, J. Chem. Soc. 127, p. 1304 (1925). But chlorination is of limited usefulness when the starting alkanaldehyde phenylhydrazone has unsubstituted active sites that will yield to chlorination at positions on the phenylhydrazone nucleus that might want to be avoided in a particular instance. Direct chlorination of an alkanaldehyde phenylhydrazone is an effective way of producing alkanoyl chloride (2,4,6-trichlorophenyl)hydrazone and alkanoyl chloride (2,4,-dichlorophenyl)hydrazone.

Among the broadly described class of alkanoyl chloride phenylhydrazones are several compounds and groups of compounds that merit particular preference for the practice of this invention. One particularly effective compound is pivaloyl chloride (2,5-dichlorophenyl)hydrazone. A preferred group of compounds is the pivaloyl chloride phenylhydrazones and particularly (dihalophenyl)hydrazones according to Formula Ia.

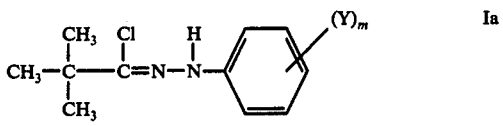

wherein Y is alkyl of from 1 to 6 carbon atoms, inclusive, halogen, trifluoromethyl, and nitro; m is an integer from 0 to 3, inclusive; there may be no more than one nitro group, the Y's may be selected independently when m is 2 or 3, and $(Y)_m$ may not be trihalo.

Another preferred group is the alkanoyl chloride (trihalophenyl)hydrazones according to Formula Ib, more particularly the 2,4,6-isomer.

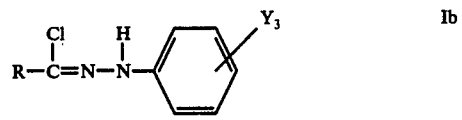

wherein R is alkyl of from 2 to 5 carbon atoms, inclusive; $Y_3$ is halogen; and the Y's may be selected independently.

Still another preferred group is the alkanoyl chloride p-halophenylhydrazones according to Formula Ic, particularly pivaloyl chloride (4-chlorophenyl)hydrazone.

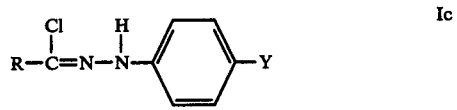

wherein R is alkyl of from 2 to 5 carbon atoms, inclusive, and Y is halogen.

Preparation I

Preparation of butyric acid (2,4,6-trichlorophenyl)hydrazide

A suspension of 9.3 g. (0.044 mole) (2,4,6-trichlorophenyl)hydrazine in 200 ml. benzene was stirred continuously while 6.3 g. (0.040 mole) butyric anhydride was added dropwise. After the butyric anhydride had all been added, the reaction mixture was heated at the reflux temperature for 2 hrs. After cooling, the reaction mixture was washed with two 40-ml. portions of water, two 40-ml. portions of 1 N sodium hydroxide, and finally with two more 40-ml. portions of water. The washed benzene solution was dried over anhydrous magnesium sulfate, and the benzene was removed by evaporation under reduced pressure. The residue thus obtained was recrystallized three times from hexane to give 8.0 g. (65% yield) of butyric acid (2,4,6-trichlorophenyl)hydrazide having a melting point of 101.5° to 102.5° C.

Analysis: Calc'd. for $C_{10}H_{11}Cl_3N_2O$: C, 42.65; H, 3.93; Cl, 37.77; N, 9.95. Found: C, 42.50; H, 3.88; Cl, 38.02; N, 10.18.

Preparation II

Following the procedure of Preparation I, but substituting (2-chloro-p-tolyl)hydrazine, (2-bromophenyl)hydrazine, (4-iodophenyl)hydrazine, (2,4,6-tribromophenyl)hydrazine, (2,4,6-triiodophenyl)hydrazine, (2,4,6-tributylphenyl)hydrazine, (3,4,5-trihexylphenyl)hydrazine, (2-methyl-4-chlorophenyl)hydrazine, (4-trifluoromethylphenyl)hydrazine, (3-isopropyl-5-methylphenyl)hydrazine, (2-chloro-6-nitro-4-trifluoromethyl)phenylhydrazine, (4-ethylphenyl)hydrazine, (3-propylphenyl)hydrazine, (3-tert.butyl-o-tolyl)hydrazine, (3,4-xylyl)hydrazine, and (3,5-diethylphenyl)hydrazine for (2,4,6-trichlorophenyl)hydrazine, there are prepared butyric acid (2-chloro-p-tolyl)hydrazide, -(2-bromophenyl)hydrazide, -(4-iodophenyl)hydrazide, -(2,4,6-tribromophenyl)hydrazide, -(2,4,6-triiodophenyl)hydrazide, -(2,4,6-tributylphenyl)-hydrazide, -(3,4,5-trihexylphenyl)hydrazide, -(2-methyl-4-chlorophenyl)hydrazide, -(4-trifluoromethylphenyl)hydrazide, -(3-isopropyl-5-methylphenyl)hydrazide, -(2-chloro-6-nitro-4-trifluoromethylphenyl)hydrazide, -(4-ethylphenyl)-hydrazide, -(3-propylphenyl)hydrazide, -(3-tert.butyl-o-tolyl)hydrazide, -(3,4-xylyl)hydrazide, and butyric acid (3,5-diethylphenyl)hydrazide, respectively.

EXAMPLE 1

Preparation of isobutyryl chloride (2,4-dichlorophenyl)hydrazone

Part A - Isobutyraldehyde phenylhydrazone

To a solution consisting of 7.2 g. (0.1 mole) isobutyraldehyde in 150 ml. chloroform was added, with stirring, 10.8 g. (0.1 mole) phenylhydrazine. The reaction flask was covered with aluminum foil and nitrogen gas was passed through the flask during the reaction. The reaction mixture was stirred for 1 hr., and then heated in order to remove, by distillation, the water produced by the reaction. About 50 ml. of a water:chloroform azeotrope was collected. Enough carbon tetrachloride was then added to bring the reaction mixture back to its original volume, thus producing a chloroform:carbon tetrachloride solution of isobutyraldehyde phenylhydrazone.

Part B - Isobutyryl chloride (2,4-dichlorophenyl)hydrazone

The chloroform:carbon tetrachloride solution of isobutyraldehyde phenylhydrazone prepared in Part A, above, was diluted to a volume of 300 ml. with carbon tetrachloride, and the air in the flask was replaced with nitrogen gas before about 14 ml. chlorine (0.3 mole) was bubbled into the reaction mixture. The mixture was stirred and kept cool (below 5° C.). After ½ hr., a sample of the reaction mixture assayed by thin layer chromatography (on silica gel with technical hexane — a mixture of isomeric hexanes boiling at 142° to 156° Fahrenheit) showed no starting material present. The reaction mixture was filtered, and the solvents were removed from the filtrate by evaporation. The residue thus obtained was dissolved in 250 ml. technical hexane and adsorbed on 1365 g. of silica gel. Elution of the column with technical hexane and evaporation of the solvent from the eluate gave 4.0 g. of isobutyryl chloride (2,4-dichlorophenyl)hydrazone as a red oil.

Analysis: Calc'd. for $C_{10}H_{11}Cl_3N_2$: C, 45.22; H, 4.17; Cl, 40.05; N, 10.55. Found: C, 45.59; H, 4.42; Cl, 40.26; N, 10.02.

EXAMPLE 2

Preparation of propionyl chloride (2,4-dichlorophenyl)hydrazone

Part A - Propionaldehyde phenylhydrazone

Following the same procedure described in Example 1, Part A, but using 100 ml. carbon tetrachloride as the solvent for 5.8 g. (0.1 mole) propionaldehyde, adding a solution of 10.8 g. (0.1 mole) phenylhydrazine in 25 ml. carbon tetrachloride, and removing the water formed by the reaction as its carbon tetrachloride azeotrope (volume of about 50 ml.), there was obtained a carbon tetrachloride solution of propionaldehyde phenylhydrazone.

Part B - Propionyl chloride (2,4-dichlorophenyl)hydrazone

Following the same procedure described in Example 1, Part B, but substituting the propionaldehyde phenylhydrazone solution prepared in Example 2, Part A, above, for the isobutyraldehyde phenylhydrazone solution, there was prepared 2.2 g. of substantially pure propionyl chloride (2,4-dichlorophenyl)hydrazone as an oil.

Analysis: Calc'd. for $C_9H_9Cl_3N_2$: C, 42.96; H, 3.60; Cl, 42.28; N, 11.13. Found: C, 43.04; H, 3.85; Cl, 43.52; N, 10.75.

EXAMPLE 3

Preparation propionyl chloride (2,4,6-trichlorophenyl)hydrazone

Part A - Propionaldehyde (2,4,6-trichlorophenyl)hydrazone

Following the procedure of Example 2, Part A, but substituting (2,4,6-trichlorophenyl)hydrazine for phenylhydrazine, there was prepared propionaldehyde (2,4,6-trichlorophenyl)hydrazone having a boiling point of 95° to 100° C. at 0.005 mm. Hg.

Analysis: Calc'd. for $C_9H_9Cl_3N_2$: C, 42.97; H, 3.61; Cl, 42.29; N, 11.14. Found: C, 42.86; H, 3.71; Cl, 42.00; N, 11.17.

Part B - Propionyl chloride (2,4,6-trichlorophenyl)hydrazone

Following the procedure of Example 1, Part B, but substituting the propionaldehyde (2,4,6-trichlorophenyl)-hydrazone prepared in Part A, above, for isobutyraldehyde phenylhydrazone, there was prepared propionyl chloride (2,4,6-trichlorophenyl)hydrazone as an oil boiling at 105° C. and 0.015 mm. Hg.

Analysis: Calc'd. for $C_9H_8Cl_4N_2$: C, 37.79; H, 2.82; Cl. 49.59; N, 9.80 Found: C, 37.99; H, 3.02; Cl, 48.59; 50.66; N, 9.79.

EXAMPLE 4

Preparation of isobutyryl chloride (2,4,6-trichlorophenyl)hydrazone

Part A - Isobutyraldehyde 2,4,6-trichlorophenylhydrazone

Following the procedure of Example 2, Part A, but substituting isobutyraldehyde for propionaldehyde and (2,4,6-trichlorophenyl)hydrazine for phenylhydrazine, there was prepared isobutyraldehyde (2,4,6-trichlorophenyl)hydrazone as an oil boiling at 115° C. and 0.05 mm. Hg.

Analysis: Calc'd. for $C_{10}H_{11}Cl_3N_2$: C, 45.22; H, 4.18; Cl, 40.05; N, 10.55. Found: C, 45.46; H, 4.29; Cl, 40.23; N, 10.19.

Part B - Isobutyryl chloride (2,4,6-trichlorophenyl)hydrazone

Following the procedure of Example 1, Part B, but substituting the isobutyraldehyde (2,4,6-trichlorophenyl)-hydrazone prepared in Part A, above, for isobutyraldehyde phenylhydrazone, there was prepared isobutyryl chloride (2,4,6-trichlorophenyl)hydrazone.

Analysis: Calc'd. for $C_{10}H_{10}Cl_4N_2$: C, 40.03; H, 3.36; Cl, 47.27; N, 9.34. Found: C, 39.94; H, 3.27; Cl, 47.85; N, 9.25.

EXAMPLE 5

Preparation of butyryl chloride (2,4,6-trichlorophenyl)hydrazone

Part A - Butyraldehyde (2,4,6-trichlorophenyl)hydrazone

Following the procedure of Example 2, Part A, but substituting butyraldehyde for propionaldehyde and 2,4,6-trichlorophenylhydrazine for phenylhydrazine, there was prepared butyraldehyde (2,4,6-trichlorophenyl)hydrazone.

Part B - Butyryl chloride (2,4,6-trichlorophenyl)hydrazone

Following the procedure of Example 1, Part B, but substituting the butyraldehyde (2,4,6-trichlorophenyl)-hydrazone prepared in Part A, above, for isobutyraldehyde phenylhydrazone, there was prepared butyryl chloride (2,4,6-trichlorophenyl)hydrazone.

Analysis: Calc'd. for $C_{10}H_{10}Cl_4N_2$: C, 40.03; H, 3.36; Cl, 47.27; N, 9.34. Found: C, 40.04; H, 3.42; Cl, 47.58; N, 8.94.

EXAMPLE 5B

Alternative preparation of butyryl chloride (2,4,6-trichlorophenyl)hydrazone

A suspension of 105.5 g. (0.50 mole) (2,4,6-trichlorophenyl)hydrazine in 550 ml. absolute ethanol was continuously stirred while 37.8 g. (0.525 mole) butyraldehyde was added dropwise. After stirring the reaction mixture for 2 hrs., 4 more grams of butyraldehyde was added and the reaction mixture was heated at the reflux temperature for 20 mins. After cooling, the ethanol was removed by evaporation under reduced pressure and any water present was removed by azeotropic distillation using carbon tetrachloride as the organic solvent. Two 500-ml. portions of carbon tetrachloride were used. After the second 500-ml. portion of carbon tetrachloride had been distilled, the dark oil that remained was dissolved in 550 ml. carbon tetrachloride, and the solution was filtered. The filtrate containing butyraldehyde (2,4,6-trichlorophenyl)hydrazone was cooled to a temperature range of 0° C. down to −10° C. and 24 ml. chlorine was bubbled into the solution accompanied by vigorous stirring. Stirring was continued for 4 hrs. at about 25° C. The reaction mixture was then filtered, and the carbon tetrachloride was removed from the filtrate by evaporation under reduced pressure. There was thus obtained 115 g. (77% yield) of butyryl chloride (2,4,6-trichlorophenyl)hydrazone as a black oil.

EXAMPLE 6

Preparation of valeryl chloride (2,4,6-trichlorophenyl)hydrazone

Part A - Valeraldehyde (2,4,6-trichlorophenyl)hydrazone

Following the procedure of Example 2, Part A, but substituting valeraldehyde for propionaldehyde and (2,4,6-trichlorophenyl)hydrazine for phenylhydrazine, there was prepared valeraldehyde (2,4,6-trichlorophenyl)hydrazone.

Analysis: Calc'd. for $C_{11}H_{13}Cl_3N_2$: C, 47.08; H, 5.03; Cl, 37.91; N, 9.98. Found: C, 47.14; H, 4.94; Cl, 38.43; N, 9.50.

Part B - Valeryl chloride (2,4,6-trichlorophenyl)hydrazone

Following the procedure of Example 1, Part B, but substituting the valeraldehyde (2,4,6-trichlorophenyl)hydrazone prepared in Part A, above, for isobutyraldehyde phenylhydrazone, there was prepared valeryl chloride (2,4,6-trichlorophenyl)hydrazone.

Analysis: Calc'd. for $C_{11}H_{12}Cl_4N_2$: C, 42.07; H, 3.85; Cl, 45.16; N, 8.92. Found: C, 41.84; H, 3.82; Cl, 45.81; N, 8.44.

EXAMPLE 7

Preparation of pivaloyl chloride (2,4,6-trichlorophenyl)hydrazone

Part A - Pivalaldehyde (2,4,6-trichlorophenyl)hydrazone

Following the procedure of Example 2, Part A, but substituting pivalaldehyde for propionaldehyde and (2,4,6-trichlorophenyl)hydrazine for phenylhydrazine, there was prepared pivalaldehyde (2,4,6-trichlorophenyl)hydrazone.

Part B - Pivaloyl chloride (2,4,6-trichlorophenyl)hydrazone

Following the procedure of Example 1, Part B, but substituting the pivalaldehyde (2,4,6-trichlorophenyl)hydrazone prepared in Part A, above, for isobutyraldehyde phenylhydrazone, there was prepared pivaloyl chloride (2,4,6-trichlorophenyl)hydrazone.

EXAMPLE 8

Preparation of pivaloyl chloride (4-chlorophenyl)hydrazone

Part A - Pivalic acid (4-chlorophenyl)hydrazide

A quantity (25.0 g.; 0.14 mole) of (4-chlorophenyl)hydrazine hydrochloride was suspended in 150 ml. of pyridine. The suspension was cooled to 0° C. and 16.9 g. (0.14 mole) of pivaloyl chloride was added with stirring. The reaction mixture was set aside at about 25° C. for 64 hrs. when 300 ml. of water was added. The precipitate that formed was collected on a filter and washed repeatedly with water, 1 N hydrochloric acid, and finally with water. The filter cake was dried under reduced pressure and 60° C. to remove water. After two recrystallizations from benzene and technical hexane there was thus obtained 24.1 g. of pivalic acid (4-chlorophenyl)hydrazide having a melting point of 137° to 138° C.

Analysis: Calc'd. for $C_{11}H_{15}ClN_2O$: C, 58.27; H, 6.67; Cl, 15.64; N, 12.36. Found: C, 58.09; H, 6.63; Cl, 15.74; N, 11.88.

Part B - Pivaloyl chloride (4-chlorophenyl)hydrazone

A quantity (15.9 g.; 0.07 mole) of pivalic acid (4-chlorophenyl)hydrazide prepared in Part A, above, and 15.3 g. (0.0735 mole) of phosphorous pentachloride were stirred together in 100 ml. of carbon tetrachloride. The suspension was heated at the reflux temperature for 15 min., when the evolution of hydrogen chloride ceased. The reaction mixture was cooled to about 5° C. and 22.2 g. (0.236 mole) of phenol was added. After the evolution of hydrogen chloride had ceased the carbon tetrachloride was removed by evaporation under reduced pressure and the residual oil was chromatographed on 1 kg. of silica gel. Elution of the column with equal parts of benzene and technical hexane and evaporation of the solvent mixture from the eluate gave pivaloyl chloride (4-chlorophenyl)hydrazone which was recrystallized from petroleum ether. The product thus obtained had a melting point of 42° to 43° C.

Analysis: Calc'd. for $C_{11}H_{14}Cl_2N_2$: C, 53.89; H, 5.76; Cl, 28.93; N, 11.43. Found: C, 53.94; H, 5.70; Cl, 28.82; N, 11.18.

EXAMPLE 9

Preparation of pivaloyl chloride (o-tolyl)-hydrazone

Part A - Pivalic acid (o-tolyl)hydrazide

Following the procedure of Example 8, Part A, but substituting (o-tolyl)hydrazine hydrochloride for (4-chlorophenyl)hydrazine hydrochloride, there was prepared pivalic acid (o-tolyl)hydrazide having a melting point of 104° to 106° C.

Analysis: Calc'd. for $C_{12}H_{18}N_2O$: C, 69.87; H, 8.80; N, 13.58. Found: C, 69.55; H, 8.59; N, 13.89.

Part B - Pivaloyl chloride (o-tolyl)hydrazone

Following the procedure of Example 8, Part B, but substituting the pivalic acid (o-tolyl)hydrazide prepared in Part A, above, for pivalic acid (4-chlorophenyl)hydrazide, there was prepared pivaloyl chloride (o-tolyl)-hydrazone.

Analysis: Calc'd. for $C_{12}H_{17}ClN_2$: C, 64.12; H, 7.62; Cl, 12.47; N, 15.79. Found: C, 64.64; H, 7.58; Cl, 12.04; N, 15.87.

EXAMPLE 10

Preparation of pivaloyl chloride phenylhydrazone

Part A - Pivalic acid phenylhydrazide

Following the procedure of Example 8, Part A, but substituting phenylhydrazine for (4-chlorophenyl)hydrazine hydrochloride and triethylamine and diethyl ether for pyridine, there was prepared pivalic acid phenylhydrazide having a melting point of 134° to 135° C.

Analysis: Calc'd. for $C_{11}H_{16}N_2O$: C, 68.72; H, 8.39; N, 14.57. Found: C, 68.58; H, 8.70; N, 14.73.

Part B - Pivaloyl chloride phenylhydrazone

Following the procedure of Example 8, Part B, but substituting the pivalic acid phenylhydrazide prepared in Part A, above, for pivalic acid (4-chlorophenyl)hydrazide, there was prepared pivaloyl chloride phenylhydrazone as an oil having a boiling point of 81° to 83° C. at 0.1 mm. Hg.

Analysis: Calc'd. for $C_{11}H_{15}ClN_2$: C, 62.70; H, 7.18; Cl, 16.83; N, 13.30. Found: C, 63.13; H, 7.13; Cl, 17.27; N, 12.85.

EXAMPLE 11

Preparation of pivaloyl chloride (2,5-dichlorophenyl)hydrazone

Part A - Pivalic acid (2,5-dichlorophenyl)hydrazide

Following the procedure of Example 8, Part A, but substituting (2,5-dichlorophenyl)hydrazine for (4-chlorophenyl)hydrazine hydrochloride, there was prepared pivalic acid (2,5-dichlorophenyl)hydrazide having a melting point of 133° to 134° C.

Analysis: Calc'd. for $C_{11}H_{14}Cl_2N_2O$: C, 50.59; H, 5.40; Cl, 27.15; N, 10.73. Found: C, 50.65; H, 5.39; Cl, 27.52; N, 10.70.

Part B - Pivaloyl chloride (2,5-dichlorophenyl)hydrazone

Following the procedure of Example 8, Part B, but substituting the pivalic acid (2,5-dichlorophenyl)hydrazide prepared in Part A, above, for pivalic acid (4-chlorophenyl)hydrazide, there was prepared pivaloyl chloride (2,5-dichlorophenyl)hydrazone having a melting point of 50° to 51° C.

Analysis: Calc'd. for $C_{11}H_{13}Cl_3N_2$: C, 47.25; H, 4.68; Cl, 38.04; N, 10.02. Found: C, 47.50; H, 4.77; Cl, 38.09; N, 10.01.

EXAMPLE 12

Preparation of pivaloyl chloride (4-nitrophenyl)hydrazone

Part A - Pivalic acid (4-nitrophenyl)hydrazide

Following the procedure of Example 8, Part A, but substituting (4-nitrophenyl)hydrazine for (4-chlorophenyl)hydrazine hydrochloride, there was prepared pivalic acid (4-nitrophenyl)hydrazide having a melting point of 168° to 170° C.

Analysis: Calc'd. for $C_{11}H_{15}N_3O_3$: C, 55.68; H, 6.37; N, 17.71. Found: C, 55.64; H, 6.33; N, 17.36.

Part B - Pivaloyl chloride (4-nitrophenyl)hydrazone

Following the procedure of Example 8, Part B, but substituting the pivalic acid (4-nitrophenyl)hydrazide prepared in Part A, above, for pivalic acid (4-chlorophenyl)hydrazide, there was prepared pivaloyl chloride (4-nitrophenyl)hydrazone having a melting point of 94.5° to 95.5° C.

Analysis: Calc'd. for $C_{11}H_{14}ClN_3O_2$: C, 51.67; H, 5.52; Cl, 13.87; N, 16.43. Found: C, 51.80; H, 5.65; Cl, 13.87; N, 16.07.

EXAMPLE 13

Following the procedure of Example 8, Part B, but substituting butyric acid (2-chloro-p-tolyl)hydrazide, -(2-bromophenyl)hydrazide, -(4-iodophenyl)hydrazide, -(2,4,6-tribromophenyl)hydrazide, -(2,4,5-triiodophenyl)hydrazide, -(2,4,5-tributylphenyl)hydrazide, -(3,4,5-trihexylphenyl)hydrazide, -(2-methyl-4-chlorophenyl)hydrazide, -(4-trifluoromethylphenyl)hydrazide, -(3-isopropyl-5-methylphenyl)hydrazide, -(2-chloro-6-nitro-4-trifluoromethylphenyl)hydrazide, -(4-ethylphenyl)hydrazide, -(3-propylphenyl)hydrazide, -(3-tert.butyl-o-tolyl)hydrazide, -(3,4-xylyl)hydrazide, and butyric acid (3,5-diethylphenyl)hydrazide for pivalic acid (4-chlorophenyl)hydrazide, there are prepared butyryl chloride (2-chloro-p-tolyl)hydrazone, -(2-bromophenyl)hydrazone, -(4-iodophenyl)hydrazone, -(2,4,6-tribromophenyl)hydrazone, -(2,4,5-triiodophenyl)hydrazone, -(2,4,5-tributylphenyl)hydrazone, -(3,4,5-trihexylphenyl)hydrazone, -(2-methyl-4-chlorophenyl)hydrazone, -(4-trifluoromethylphenyl)hydrazone, -(3-isopropyl-5-methylphenyl)hydrazone, -(2-chloro-6-nitro-4-trifluoromethylphenyl)hydrazone, -(4-ethylphenyl)hydrazone, -(3-propylphenyl)hydrazone, -(3-tert.butyl-o-tolyl)hydrazone, -(3,4-xylyl)hydrazone, and butyryl chloride (3,5-diethylphenyl)hydrazone, respectively.

The insecticidal and miticidal, and herbicidal alkanoyl chloride phenylhydrazones of Formula I can be used as the pure compounds, such as those described in the Examples, or as technical grade compounds from commercial production; but for practical reasons, the compounds are preferably formulated as insecticidal and miticidal, and herbicidal compositions. More particularly, the alkanoyl chloride phenylhydrazones are preferably formulated with a diluent carrier. There are many different kinds of diluent carriers known to be useful for preparing insecticidal and miticidal, and herbicidal compositions. Dispersible insecticide and miticide, and herbicide carriers are commonly used in the art, but non-dispersible carrier matrices are also used. The compositions may or may not include adjuvants such as wetting agents, emulsifying agents, stickers, and other components that indirectly promote efficacy.

Illustratively, dispersible compositions useful against insects and mites and weed plants can be formulated as dusts, wettable powders, emulsifiable concentrates, aqueous dispersions, solutions, and flowable creams for application to animals, soils, plants and other places where control of insects and mites, or weeds is desired. Compositions suitable for uniform dispersive application can be made; and granular compositions can be made for application to soil or on surfaces. Moreover, the alkanoyl chloride phenylhydrazones of the invention can be the sole active agent in a composition or other insecticidal, miticidal, fungicidal, virucidal, bactericidal, herbicidal, or synergistic components may be included.

The alkanoyl chloride phenylhydrazones can be formulated as dusts by preparing a mixture of the compound and a pulverulent carrier. Dusts can be prepared by dissolving an alkanoyl chloride phenylhydrazone in a volatile solvent such as methylene chloride, mixing the solution with a pulverulent carrier and evaporating the solvent. The mixture of pulverulent carrier and active ingredient can be ground to a suitable particle size in a ball mill, a hammermill, or by air-blast micronization. A suitable ultimate particle size is less than 60 microns. Preferably, 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling insects and mites over wide areas when applied by airplane. They are also indicated for application to relatively inaccessible areas and to the skin of poultry and hairy animals.

Representative suitable pulverulent carriers include the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, calcium carbonates, sulfur, silica and silicates; chemically modified minerals such as washed bentonite, precipitated calcium phosphate, precipitated calcium silicate, synthetic magnesium silicate, and colloidal silica; and organic flours such as wood, walnut shell, soybean, cottonseed, and tobacco flours, and free-flowing, hydrophobic starches.

The proportions of pulverulent carrier and alkanoyl chloride phenylhydrazone can vary over a wide range depending upon the insects or mites, or weeds to be controlled and the conditions of treatment. Dust formulations can contain up to about 90% (on a weight basis) of the active ingredient. Dusts having as little as 0.001% of the active ingredient can be used, but a generally preferred proportion is from about 0.50% to about 20% of active ingredient.

The dispersible powder formulations of this invention are prepared by incorporating a surfactant in a dust composition prepared as described above. When about 0.1% to about 12% of a surfactant is incorporated in a dust, the dispersible powder thus obtained is particularly adapted for further admixture with water for spraying on inanimate matter and products, weeds, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 10% to about 80% of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylenesorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder compositions can be formulated with a mixture of surfactants of the types indicated if desired.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient. The resulting formulation has the following percentage composition (parts herein are by weight unless otherwise specified).

| | |
|---|---|
| Active ingredient | 25% |
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to insects or mites, insect or mite habitats, insect or mite foods, and to weeds for the control of these undesired forms of life.

If desired, dispersants such as methyl cellulose, polyvinyl alcohol, sodium ligninsulfonates, and the like can be included in the dispersible powder formulations of this invention. Adhesive or sticking agents such as vegetable oils, naturally occurring gums, casein, and others can also be included. Corrosion inhibitors such as epichlorohydrin and anti-foaming agents such as stearic acid can also be included.

The insecticidal and miticidal, and herbicidal alkanoyl chloride phenylhydrazones of this invention can be applied to insects, mites, weeds, objects, or a situs in aqueous sprays without a solid carrier. Since, however, the compounds themselves are relatively insoluble in water they are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used the solvent carrier will dissolve in the water and any excess alkanoyl chloride phenylhydrazone will be thrown out of solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which alkanoyl chloride phenylhydrazones are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for applying to insects and mites, and weeds.

The emulsifiable concentrates of the invention are prepared, therefore, by dissolving the active ingredient and a surfactnat in a substantially water-immiscible solvent carrier (i.e., a solvent carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40% A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

The concentrate compositions of the invention which are intended for use in the form of aqueous dispersions or emulsions can also comprise a humectant, that is to say, an agent which will delay the drying of the composition in contact with material to which it has been applied. Suitable humectants include glycerol, diethylene glycol, solubilized lignins, such as calcium ligninsulfonate, and the like.

The granular compositions of this invention are convenient for application to soil when persistence is desired. Granulars are readily applied broadcast or by localized, e.g., in-the-row applications. The individual granules may be any desired size from 30 to 60 mesh up to 10 to 20 mesh, or even larger. Granulars are prepared by dissolving the active compound in a solvent such as methylene chloride, xylene, or acetone and applying the solution to a quantity of a granulated absorbent carrier. Representative granulated absorbent carriers include ground corn cobs, ground walnut shells, ground peanut hulls, and the like. If desired, the impregnated granulated absorbent carrier can be coated with a material that will preserve the integrity of the granular until it is applied to an object or situs favorable for release of the active ingredient.

The rates of application to insects, mites, weeds, objects, or situs will depend upon the species of insects, mites, or weeds to be controlled, the presence or absence of desirable living organisms, temperature conditions of treatment, and the method and efficiency of application. In general, insecticidal and miticidal, and herbicidal activity is obtained when the compounds are applied at concentrations of about 10 to about 6000 ppm, preferably at concentrations of about 30 to about 4000 ppm.

The compositions containing alkanoyl chloride phenylhydrazones according to the invention, can be applied to insects, mites, weeds, objects or a situs by conventional methods. For example, an area of soil, a building, or plants can be treated by spraying wettable powder suspensions, emulsions, or solutions from power sprayers or from hand-operated knapsack sprayers. Dips can be used for livestock. Dusts can be applied by power dusters, or by hand-operated dusters. Creams and ointment formulations can be applied to skin or objects for prolonged protection from insects or mites.

The active compounds of the invention can also be formulated in relatively dilute proportions in a dispersible insecticide carrier for household applications. Thus, the active compounds can be formulated in dusts having from about 0.1% to 5.0% active ingredient with a dusting powder as hereinbefore described, and in solutions containing from about 0.01% to about 5.0% active ingredient with deodorized kerosene for aerosol applications.

It will of course be appreciated that the conditions encountered when applying the method and compositions of this invention to actual practice can vary widely. Included among the variables that may be encountered are the degree of infestation by insects, mites, or weeds, the particular pest to be controlled, the particular situs being treated, the age or degree of development of animals or plants, the prevailing weather conditions, such as temperature, relative humidity, rainfall, dews, and so forth.

The compounds of Formula I are effective pesticides that can be used to control invertebrate pests in agriculture, in industry, and around the home. The compounds have been found to be active against invertebrate animals of the Phylum Arthropoda, illustratively Class Insecta, for example, order Coleoptera, more specifically, the cotton boll weevil (*Anthonomus grandis* Boheman), the confused flour beetle (*Tribolium confusum* Jacquelin de Val), and the Mexican bean beetle (*Epilachna verivestis* Mulsant), order Diptera, more specifically, the housefly (*Musca domestica* Linnaeus), order Orthoptera, more specifically, the house cricket (*Acheta domesticus* Linnaeus), and the German cockroach (*Blatella germanica* Linnaeus), and order Lepidoptera, more specifically, the Southern armyworm (*Prodenia eridania* Cramer), and Class Arachnida, for example, order Acarina, more specifically the two-spotted spider mite (*Tetranychus urticae* Koch).

Efficacy against invertebrate pests has been demonstrated at concentrations of 1000, 500, 100, 50 and even 10 ppm depending upon the specific insect or mite used. Some invertebrate animal pests will be more sensitive to the compounds than others, and others might be quite resistant. In general, the compounds of Formula I are used at concentrations ranging from about 30 to about 6000 ppm.

One particularly active group is the alkanoyl chloride (trihalophenyl)hydrazones according to Formula Ib, more particularly, the alkanoyl chloride (2,4,6-trihalophenyl)-hydrazones. Another particularly active group is the pivaloyl chloride phenylhydrazones according to Formula Ia. Some of the specific preferred compounds are butyryl chloride 2,4,6-trichlorophenylhydrazone, propionyl chloride 2,4,6-trichlorophenylhydrazone, valeryl chloride 2,4,6-trichlorophenylhydrazone, isobutyryl chloride 2,4,6-trichlorophenylhydrazone, pivaloyl chloride 2,5-dichlorophenylhydrazone, pivaloyl chloride (4-chlorophenyl)hydrazone, and pivaloyl chloride phenylhydrazone.

The alkanoyl chloride phenylhydrazones of this invention (compounds of Formula I) are active against plants and kill certain plants selectively. Such active compounds can be used as herbicides. Representative weeds against which herbicidal activity has been found are crabgrass (*Digitaria sanguinalis*), yellow foxtail (*Setaria glauca*), wild oats (*Avena fatua L.*) bindweed (*Convolvulus arvensis L.*), Johnson grass (*Sorghum helepense*

L.), buckhorn plantain (*Plantago lanceolata* L.), and curly dock (*Rumex crispus* L.).

I claim:

1. New alkanoyl chloride (trihalophenyl)hydrazones of the formula:

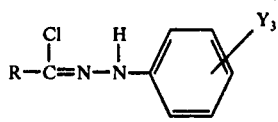

wherein R is alkyl of from 2 to 5 carbon atoms, inclusive; Y is halogen, and the Y's may be selected independently.

2. New alkanoyl chloride (trichlorophenyl)hydrazones according to claim 1 wherein each Y is chlorine.

3. New alkanoyl chloride (trichlorophenyl)hydrazones according to claim 2 wherein the chlorine atoms are oriented 2,4,6-.

4. New pivaloyl chloride phenylhydrazones of the formula:

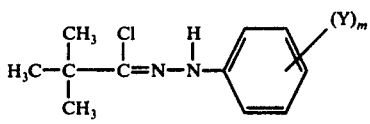

wherein Y is alkyl of from 1 to 6 carbon atoms, inclusive, halogen, trifluoromethyl, and nitro; m is an integer from 0 to 3, inclusive; there may be no more than one nitro group, the Y's may be selected independently when m is 2 or 3, and $(Y)_m$ may not be trihalo.

5. New pivaloyl chloride (dichlorophenyl)hydrazones according to claim 4 wherein m is 2.

6. Pivaloyl chloride (2,5-dichlorophenyl)hydrazone according to claim 5.

7. Pivaloyl chloride (4-chlorophenyl)hydrazone according to claim 4.

8. Propionyl chloride (2,4,6-trichlorophenyl)hydrazone according to claim 3.

9. Isobutyryl chloride (2,4,6-trichlorophenyl)hydrazone according to claim 3.

10. Butyryl chloride (2,4,6-trichlorophenyl)hydrazone according to claim 3.

11. Valeryl chloride (2,4,6-trichlorophenyl)hydrazone according to claim 3.

12. Pivaloyl chloride (2,4,6-trichlorophenyl)hydrazone according to claim 3.

13. New pivaloyl chloride (alkylphenyl)hydrazones according to claim 4.

14. Pivaloyl chloride o-tolylhydrazone according to claim 13.

15. The compound pivaloyl chloride phenylhydrazone according to claim 4.

16. New pivaloyl chloride (nitrophenyl)hydrazones according to claim 4.

17. Pivaloyl chloride (4-nitrophenyl)hydrazone according to claim 16.

18. A phenylhydrazone derivative of the formula:

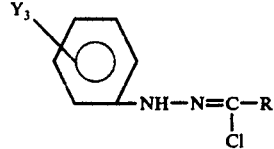

wherein R represents alkyl of 2 to 5 carbon atoms and Y is halogen.

19. A compound of claim 18 wherein Y is chlorine.

20. A compound of claim 18 wherein Y is iodo, and R is $CH_3-CH_2-CH_2-$, i.e., butyryl chloride (2,4,5-triiodophenyl)hydrazone.

* * * * *